(12) United States Patent
Russo

(10) Patent No.: US 10,653,507 B2
(45) Date of Patent: May 19, 2020

(54) EXPANDING ABSORBABLE TACK

(71) Applicant: Covidien LP, Mansfield, MA (US)

(72) Inventor: Mark Russo, Plantsville, CT (US)

(73) Assignee: Covidien LP, Mansfield, MA (US)

(*) Notice: Subject to any disclaimer, the term of this patent is extended or adjusted under 35 U.S.C. 154(b) by 272 days.

(21) Appl. No.: 15/428,420

(22) Filed: Feb. 9, 2017

(65) Prior Publication Data

US 2017/0151048 A1 Jun. 1, 2017

Related U.S. Application Data

(63) Continuation of application No. 14/286,142, filed on May 23, 2014, now abandoned.

(Continued)

(51) Int. Cl.
*A61F 2/00* (2006.01)
*A61B 17/068* (2006.01)
*A61B 17/064* (2006.01)

(52) U.S. Cl.
CPC .......... *A61F 2/0063* (2013.01); *A61B 17/064* (2013.01); *A61B 17/068* (2013.01);
(Continued)

(58) Field of Classification Search
CPC .... A61B 2017/0648; A61B 2017/0647; A61B 17/064; A61B 17/068; A61B 17/8615; A61B 17/862; A61B 17/861; A61B 17/8605; A61B 17/0401; A61B 2017/0409; A61B 17/7258; A61B 17/7266; A61B 17/7275; A61F 2/0063; A61F 2220/0016; F16B 23/00; F16B 23/0007; F16B 35/04; F16B 35/06
See application file for complete search history.

(56) References Cited

U.S. PATENT DOCUMENTS 3,596,528 A 8/1971 Dittrich et al.
3,866,510 A 2/1975 Eibes et al.
(Continued)

FOREIGN PATENT DOCUMENTS

CN 104337555 A 2/2015
DE 10300787 A1 9/2004
(Continued)

OTHER PUBLICATIONS

Australian Examination Report issued in corresponding Australian Application No. 2014202970 dated Mar. 9, 2018.
(Continued)

*Primary Examiner* — Diane D Yabut
*Assistant Examiner* — Majid Jamialahmadi
(74) *Attorney, Agent, or Firm* — Carter, DeLuca & Farrell LLP

(57) ABSTRACT

A surgical fastener includes a head section and a tissue snaring section. The head section includes an arm member pivotably disposed on an outer surface of the head section. The tissue snaring section defines a longitudinal axis and extends away from the head section. At least one helical thread defined along an outer surface of the tissue snaring section. The tissue snaring section is configured to rotate about the longitudinal axis in a first radial direction, and the arm member is configured pivot outwardly from the head section in the first radial direction.

17 Claims, 4 Drawing Sheets

Related U.S. Application Data

(60) Provisional application No. 61/857,709, filed on Jul. 24, 2013.

(52) U.S. Cl.
CPC .......... *A61B 2017/0648* (2013.01); *A61F 2002/0072* (2013.01)

(56) References Cited

U.S. PATENT DOCUMENTS

| | | |
|---|---|---|
| 4,350,491 A | 9/1982 | Steuer |
| 4,884,572 A | 12/1989 | Bays et al. |
| 5,085,661 A | 2/1992 | Moss |
| 5,171,247 A | 12/1992 | Hughett et al. |
| 5,171,249 A | 12/1992 | Stefanchik et al. |
| 5,176,306 A | 1/1993 | Heimerl et al. |
| 5,203,864 A | 4/1993 | Phillips |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,312,023 A | 5/1994 | Green et al. |
| 5,330,487 A | 7/1994 | Thornton et al. |
| 5,344,061 A | 9/1994 | Crainich |
| 5,356,064 A | 10/1994 | Green et al. |
| 5,381,943 A | 1/1995 | Allen et al. |
| 5,382,254 A | 1/1995 | McGarry et al. |
| 5,398,861 A | 3/1995 | Green |
| 5,403,327 A | 4/1995 | Thornton et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,709,692 A | 1/1998 | Mollenauer et al. |
| 5,725,541 A | 3/1998 | Anspach, III et al. |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,810,882 A | 9/1998 | Bolduc et al. |
| 5,824,008 A | 10/1998 | Bolduc et al. |
| 5,830,221 A | 11/1998 | Stein et al. |
| 5,840,078 A * | 11/1998 | Yerys .............. A61B 17/17 606/151 |
| 5,843,087 A | 12/1998 | Jensen et al. |
| 5,893,856 A | 4/1999 | Jacob et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,757 B1 | 6/2002 | Moore, III et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,447,524 B1 | 9/2002 | Knodel et al. |
| 6,450,391 B1 | 9/2002 | Kayan et al. |
| 6,457,625 B1 | 10/2002 | Tormala et al. |
| 6,544,273 B1 | 4/2003 | Harari et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,913,607 B2 | 7/2005 | Ainsworth et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,128,754 B2 | 10/2006 | Bolduc |
| 7,147,657 B2 | 12/2006 | Chiang et al. |
| 7,182,769 B2 | 2/2007 | Ainsworth et al. |
| 7,204,847 B1 | 4/2007 | Gambale |
| 7,261,716 B2 | 8/2007 | Strobel et al. |
| 7,491,232 B2 | 2/2009 | Bolduc et al. |
| 7,544,198 B2 | 6/2009 | Parodi |
| 7,591,842 B2 | 9/2009 | Parodi |
| 7,632,287 B2 | 12/2009 | Baker et al. |
| 7,637,932 B2 | 12/2009 | Bolduc et al. |
| 7,670,362 B2 | 3/2010 | Zergiebel |

(56) References Cited

U.S. PATENT DOCUMENTS

| | | |
|---|---|---|
| 7,758,612 B2 | 7/2010 | Shipp |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,034,076 B2 | 10/2011 | Criscuolo et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,343,176 B2 | 1/2013 | Criscuolo et al. |
| 8,343,184 B2 | 1/2013 | Blier |
| 8,382,778 B2 | 2/2013 | Criscuolo et al. |
| 8,414,627 B2 | 4/2013 | Corradi et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,685,044 B2 | 4/2014 | Bolduc et al. |
| 8,690,897 B2 | 4/2014 | Bolduc |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,920,439 B2 | 12/2014 | Cardinale et al. |
| 8,926,637 B2 | 1/2015 | Zergiebel |
| 8,968,311 B2 | 3/2015 | Allen, IV et al. |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,274 B2 | 6/2016 | Zergiebel |
| 9,402,623 B2 | 8/2016 | Kayan |
| 9,486,218 B2 | 11/2016 | Criscuolo et al. |
| 9,526,498 B2 | 12/2016 | Reed |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,801,633 B2 | 10/2017 | Sholev et al. |
| 9,867,620 B2 | 1/2018 | Fischvogt et al. |
| 9,987,010 B2 | 6/2018 | Zergiebel |
| 10,070,860 B2 | 9/2018 | Zergiebel |
| 2002/0082622 A1 | 6/2002 | Kane |
| 2003/0009441 A1 | 1/2003 | Holsten et al. |
| 2003/0114839 A1 | 6/2003 | Looper et al. |
| 2004/0092937 A1 | 5/2004 | Criscuolo et al. |
| 2004/0111089 A1 | 6/2004 | Stevens et al. |
| 2004/0127916 A1 | 7/2004 | Bolduc et al. |
| 2004/0181222 A1 | 9/2004 | Culbert et al. |
| 2004/0193217 A1 | 9/2004 | Lubbers et al. |
| 2004/0204723 A1 | 10/2004 | Kayan |
| 2004/0243139 A1 | 12/2004 | Lewis et al. |
| 2006/0100629 A1 | 5/2006 | Lee |
| 2006/0129152 A1 | 6/2006 | Shipp |
| 2006/0129154 A1* | 6/2006 | Shipp .................. A61B 17/0644 606/301 |
| 2006/0167481 A1 | 7/2006 | Baker et al. |
| 2006/0173470 A1 | 8/2006 | Oray et al. |
| 2006/0212049 A1 | 9/2006 | Mohiuddin |
| 2007/0005082 A1 | 1/2007 | Kraemer et al. |
| 2007/0038220 A1 | 2/2007 | Shipp |
| 2007/0088390 A1* | 4/2007 | Paz .................... A61B 17/0401 606/232 |
| 2007/0162030 A1 | 7/2007 | Aranyi et al. |
| 2007/0191870 A1 | 8/2007 | Baker et al. |
| 2007/0293879 A1 | 12/2007 | Baker et al. |
| 2008/0086154 A1 | 4/2008 | Taylor et al. |
| 2008/0097523 A1 | 4/2008 | Bolduc et al. |
| 2008/0147113 A1 | 6/2008 | Nobis et al. |
| 2008/0188868 A1 | 8/2008 | Weitzner et al. |
| 2008/0243106 A1 | 10/2008 | Coe et al. |
| 2008/0281336 A1 | 11/2008 | Zergiebel |
| 2008/0312687 A1 | 12/2008 | Blier |
| 2009/0012356 A1 | 1/2009 | Dann et al. |
| 2009/0030434 A1 | 1/2009 | Paz et al. |
| 2009/0112234 A1 | 4/2009 | Crainich et al. |
| 2009/0118747 A1 | 5/2009 | Bettuchi et al. |
| 2009/0118776 A1 | 5/2009 | Kelsch et al. |
| 2009/0188965 A1 | 7/2009 | Levin et al. |
| 2009/0259235 A1 | 10/2009 | Doucet et al. |
| 2010/0023028 A1 | 1/2010 | Baker et al. |
| 2010/0030262 A1 | 2/2010 | McLean et al. |
| 2010/0049221 A1 | 2/2010 | Baker et al. |
| 2010/0114127 A1 | 5/2010 | Lewallen |
| 2010/0217330 A1* | 8/2010 | Phan .................... A61B 17/8605 606/301 |
| 2010/0270354 A1 | 10/2010 | Rimer et al. |
| 2010/0292710 A1 | 11/2010 | Daniel et al. |
| 2010/0292713 A1 | 11/2010 | Cohn et al. |
| 2010/0292715 A1 | 11/2010 | Nering et al. |
| 2011/0022065 A1 | 1/2011 | Shipp |
| 2011/0042441 A1 | 2/2011 | Shelton, IV et al. |
| 2011/0060349 A1 | 3/2011 | Cheng et al. |
| 2011/0071578 A1 | 3/2011 | Colesanti et al. |
| 2011/0079627 A1 | 4/2011 | Cardinale et al. |
| 2011/0087240 A1 | 4/2011 | Shipp |
| 2011/0204120 A1 | 8/2011 | Crainich |
| 2011/0282401 A1 | 11/2011 | Corradi et al. |
| 2011/0295269 A1 | 12/2011 | Swensgard et al. |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2013/0018392 A1 | 1/2013 | Zergiebel |
| 2013/0110088 A1 | 5/2013 | Wenchell |
| 2013/0131700 A1 | 5/2013 | Criscuolo et al. |
| 2013/0197591 A1 | 8/2013 | Corradi et al. |
| 2014/0114329 A1 | 4/2014 | Zergiebel |
| 2014/0121684 A1 | 5/2014 | Criscuolo et al. |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0018847 A1 | 1/2015 | Criscuolo et al. |
| 2015/0032130 A1 | 1/2015 | Russo |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0066971 A1 | 3/2016 | Corradi et al. |

(56) References Cited

U.S. PATENT DOCUMENTS

| | | |
|---|---|---|
| 2016/0074034 A1 | 3/2016 | Shipp |
| 2016/0135807 A1 | 5/2016 | Zergiebel |
| 2016/0166255 A1 | 6/2016 | Fischvogt |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniffin et al. |
| 2017/0042657 A1 | 2/2017 | Criscuolo et al. |
| 2017/0128068 A1 | 5/2017 | Zhang et al. |
| 2017/0151048 A1 | 6/2017 | Russo |
| 2017/0231631 A1 | 8/2017 | Abuzaina et al. |
| 2017/0265859 A1 | 9/2017 | Sniffin et al. |
| 2018/0042591 A1 | 2/2018 | Russo et al. |
| 2018/0116670 A1 | 5/2018 | Fischvogt et al. |

FOREIGN PATENT DOCUMENTS

| | | |
|---|---|---|
| DE | 10 2010 015009 A1 | 10/2011 |
| EP | 0374088 A1 | 6/1990 |
| EP | 0834280 A1 | 4/1998 |
| EP | 1273272 A2 | 1/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| EP | 2853202 A2 | 4/2015 |
| JP | 09149906 | 6/1997 |
| WO | 00/16701 A1 | 3/2000 |
| WO | 2002/034140 A2 | 5/2002 |
| WO | 2003/034925 A2 | 5/2003 |
| WO | 2003/103507 A2 | 12/2003 |
| WO | 2004/112841 A2 | 12/2004 |
| WO | 2005004727 A1 | 1/2005 |
| WO | 2009/039506 A1 | 3/2009 |
| WO | 2012/064692 A2 | 5/2012 |
| WO | 2013/046115 A1 | 4/2013 |
| WO | 2015/131362 A1 | 9/2015 |

OTHER PUBLICATIONS

European Office Action corresponding to Patent Application EP 14 15 8946.5 dated Apr. 26, 2018.
Japanese Office Action corresponding to Patent Application JP 2014-132105 dated May 1, 2018.
Japanese Office Action corresponding to Patent Application JP 2014-047708 dated May 14, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.
European Office Action issued in corresponding European Application No. 14178107.0 dated Oct. 12, 2017.
Extended European Search Report corresponding to counterpart Int'l, Appln. No. EP 14 81 7036.8 dated Feb. 2, 2017.
European Office Action corresponding to counterpart Int'l, Appln. No. EP 14 19 7885.8 dated Feb. 7, 2017.
Chinese First Office Action corresponding to counterpart Int'l Appln. No. CN 201410090675 dated Feb. 28, 2017.
European Office Action corresponding to counterpart Int'l Appln. No. EP 14 15 1663.3 dated May 10, 2017.
Extended European Search Report corresponding to counterpart Int'l Appln. No. EP 17 15 7259.7 dated May 10, 2017.
Australian Examination Report No. 1 corresponding to counterpart Int'l Appln. No. AU 2014200071 dated Jun. 20, 2017.
Australian Examination Report No. 1 corresponding to counterpart Int'l Appln. No. AU 2014201338 dated Jul. 10, 2017.
Chinese First Office Action corresponding to Chinese Patent Appln. No. 201480037169.2 dated Jun. 29, 2017.
Chinese First Office Action corresponding to Chinese Patent Appln. No. 201410418879.1 dated Jun. 29, 2017.
Australian Examination Report No. 1 corresponding to Australian Patent Appln. No. 2014200870 dated Oct. 26, 2017.
Chinese Second Office Action corresponding to Chinese Patent Appln. No. 201410090675 dated Nov. 6, 2017.
Japanese Office Action corresponding to Japanese Patent Appln. No. 2014-048652 dated Nov. 14, 2017.
Japanese Office Action corresponding to Japanese Patent Appln. No. 2014-047708 dated Nov. 14, 2017.
Chinese Second Office Action corresponding to Chinese Patent Appln. No. 2014103063407 dated Feb. 1, 2018.
Japanese Office Action corresponding to Japanese Patent Appln. No. 2014-048652 dated Mar. 15, 2018.
Chinese Second Office Action corresponding to Chinese Patent Appln. No. 201480077682.4 dated Mar. 21, 2018.
Australian Examination Report No. 1 corresponding to Australian Patent Appln. No. 2014202972 dated Mar. 27, 2018.
Extended European Search Report corresponding to EP No. 10 01 2659.8, completed Dec. 21, 2010 and dated Jan. 3, 2011; 3 pages.
Extended European Search Report corresponding to EP No. 10 01 2646.5, completed Feb. 11, 2011 and dated Feb. 22, 2011; 10 pages.
Extended European Search Report corresponding to EP No. 11 25 0549.0, completed Sep. 9, 2013 and dated Sep. 17, 2013; 9 pages.
Extended European Search Report corresponding to EP 14 15 9394.7, completed Apr. 16, 2014 and dated Apr. 29, 2014; 8 pages.
Extended European Search Report corresponding to EP 14 17 8107.0, completed Nov. 24, 2014 and dated Dec. 3, 2014; 5 pages.
Extended European Search Report corresponding to EP 14 15 8946.5, completed Jun. 20, 2014 and dated Jul. 8, 2014; (9 pp).
Extended European Search Report corresponding to EP 14 17 8107.0, completed Nov. 24, 2014 and dated Dec. 3, 2014; (5 pp).
Extended European Search Report corresponding to EP 14 17 4656.0, completed Jan. 16, 2015 and dated Jan. 26, 2015; (7 pp).
Extended European Search Report corresponding to EP 14 18 4907.5, completed Jan. 12, 2015 and dated Jan. 27, 2015; (9 pp).
Extended European Search Report corresponding to counterpart application EP 14 19 7885.8 dated Apr. 30, 2015; 9pp.
Extended European Search Report corresponding to counterpart application EP 14 18 1900.3 dated Apr. 9, 2015; 7pp.
Extended European Search Report corresponding to European Appln. No. 16198333.3 dated Mar. 15, 2017.
Extended European Search Report corresponding to Int'l, Application No. EP 14 15 1663.3 dated Jun. 7, 2016.
Chinese Office Action issued in Chinese Application No. 2014103559671 dated May 25, 2018.
Chinese Office Action issued in corresponding Chinese Application No. 2014103559671 dated Jun. 13, 2017.
Chinese Office Action issued in corresponding Chinese Office Action 201610994981.5 dated May 8, 2019, 13 pages.
Chinese Office Action dated Sep. 19, 2019 issued in corresponding CN Appln. No. 201610994981.5.

* cited by examiner

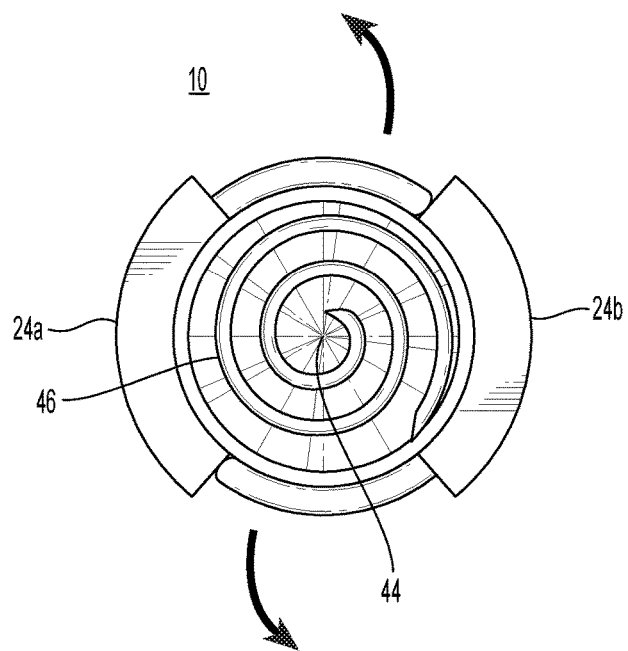
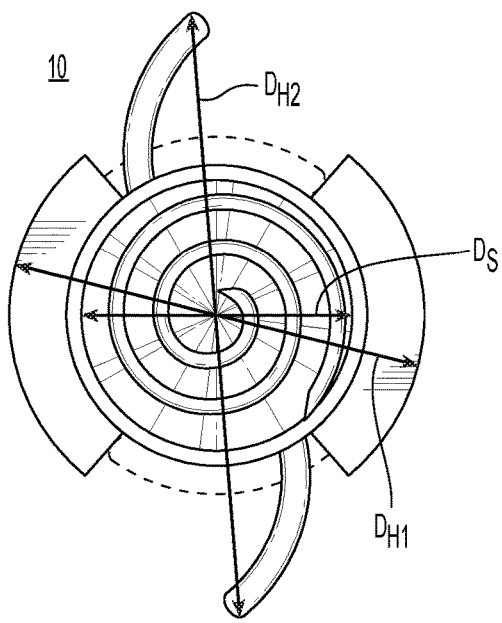
FIG. 3A
FIG. 3B
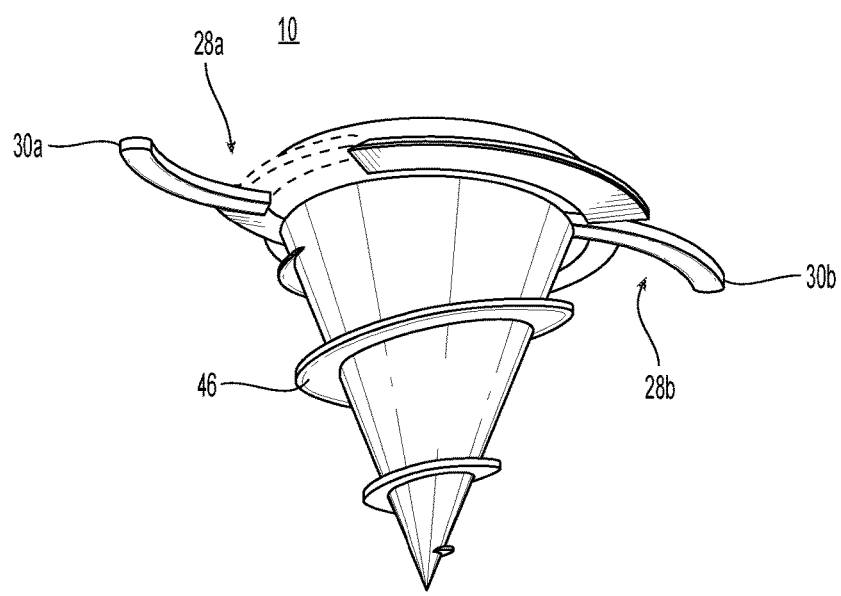
FIG. 4

EXPANDING ABSORBABLE TACK

CROSS REFERENCE TO RELATED APPLICATIONS

This application is a continuation of U.S. patent application Ser. No. 14/286,142, filed May 23, 2014, which claims the benefit of U.S. Provisional Patent Application No. 61/857,709, filed Jul. 24, 2013, the entire contents of each of which are incorporated by reference herein.

BACKGROUND OF THE INVENTION

1. Technical Field

The present disclosure relates to surgical fasteners, and more particularly, to surgical features including an arm member and associated methods of applying.

2. Description of Related Art

In hernias, such as direct or indirect inguinal hernias, a part of the intestine protrudes through a defect in the support abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

In contrast, minimally invasive, e.g., endoscopic or laparoscopic, surgical procedures are currently available to repair a hernia. In laparoscopic procedures, surgery is performed in the abdomen through a small incision while in endoscopic procedures, surgery is performed through narrow endoscopic tubes or cannulas inserted through small incisions in the body.

Currently, minimally invasive surgical techniques for hernia repair utilize surgical fasteners, e.g., surgical tacks, staples, and clips, to secure the mesh to the tissue to provide reinforcement to the repair and structure for encouraging tissue ingrowth. Surgical fasteners may be deployed with a surgical fastener applier through a mesh and into tissue below.

Challenges may be presented in affixing a mesh over a hernial defect with surgical fasteners, e.g., in instances involving irregular or uneven surface geometries, or in situations when internal body structures are subject to movement and shifting. However, it is desirable to minimize the number and size of surgical fasteners deployed through a mesh to minimize trauma to the tissue below. Accordingly, it would be desirable to provide a surgical fastener that is configured with optimized mesh retention properties, while minimizing the portion or size of the surgical fastener inserted into tissue.

SUMMARY OF THE INVENTION

According to one aspect of the present disclosure, a surgical fastener is disclosed, and includes a head section and a tissue snaring section. The head section includes an arm member pivotably disposed on an outer surface of the head section. The tissue snaring section defines a longitudinal axis and extends away from the head section. At least one helical thread defined along an outer surface of the tissue snaring section. The tissue snaring section is configured to rotate about the longitudinal axis in a first radial direction, and the arm member is configured pivot outwardly from the head section in the first radial direction.

In one aspect of the present disclosure, the head section includes a threaded section. The arm member may be disposed radially adjacent the threaded section of the head section. In another aspect of the present disclosure, the arm member is biased toward a radially outward position. According to another aspect of the present disclosure, the arm member has an arcuate configuration.

According to another aspect of the present disclosure, a surgical fastener is disclosed, and includes a head section and a tissue snaring section. The head section includes an arm member pivotably disposed on an outer surface of the head section. The tissue snaring section defines a longitudinal axis and extends away from the head section. At least one helical thread is defined along an outer surface of the tissue snaring section. The arm member is configured such that, in a first condition of the surgical fastener, the arm member is disposed radially inward with respect to the outer surface of the head section such that a first transverse head section diameter is defined, and in a second condition of the surgical fastener, the arm member is disposed radially outward with respect to the outer surface of the head section such that a different, second transverse head section diameter is defined.

In one aspect of the present disclosure, the head section includes a threaded section. The arm member may be disposed radially adjacent the threaded section of the head section. In another aspect of the present disclosure, the arm member is biased toward a radially outward position. According to another aspect of the present disclosure, the arm member has an arcuate configuration. In the first configuration, the arcuate configuration of the arm member may approximate the curvature of a surface of the head section.

According to another aspect of the present disclosure, the arm member is configured to pivot between and including 0 degrees and 180 degrees. In one aspect of the present disclosure, the surgical fastener is configured to be disposed within a delivery device, and is configured to be maintained in the first condition by arm with the delivery device.

According to another aspect of the present disclosure, a method of deploying a surgical fastener including a head section including an arm member pivotably disposed thereon and a tissue snaring section extending away from the head section is disclosed. The method includes loading the surgical fastener in a delivery device such that the arm member of the head section is disposed in a first, radially constrained configuration, and advancing the surgical fastener out of the delivery device such that the arm member pivots radially outward with respect to the outer surface of the head section in a second, deployed configuration.

In another aspect of the present disclosure, the method includes the step of advancing the surgical fastener includes actuating the delivery device. According to another aspect of the present disclosure, the method further includes further the step of advancing the surgical fastener through a mesh and into tissue such that, in the deployed configuration, the mesh is compressed against tissue.

BRIEF DESCRIPTION OF THE DRAWINGS

Embodiments of the present disclosure will be appreciated by reference to the drawings, wherein:

FIG. 3A is a bottom plan view of the surgical fastener of FIG. 1 in the first configuration;

FIG. 3B is a bottom plan view of the surgical fastener of FIG. 1 in the second configuration;

FIG. 4 is a side perspective view of the surgical fastener of FIG. 1 shown transitioning between the first configuration and the second configuration;

DETAILED DESCRIPTION

Figure 1:
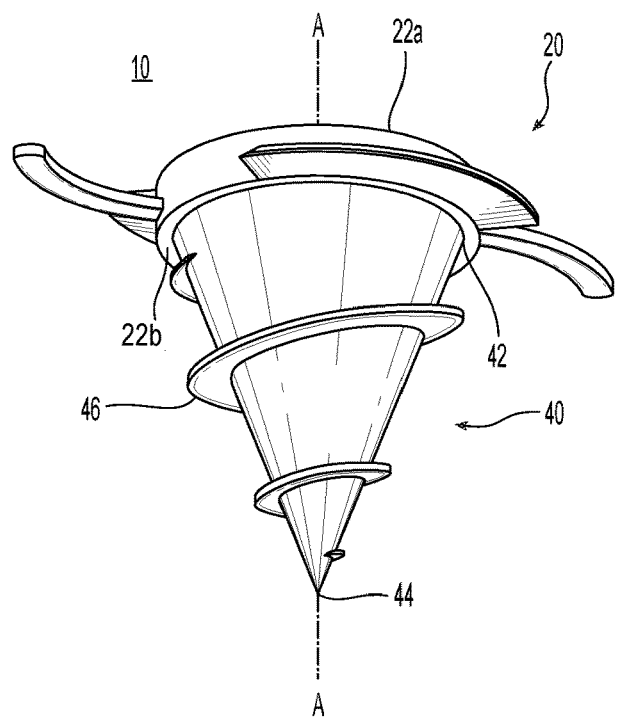
FIG. 1 is a side, perspective view of a surgical fastener according to the present disclosure.
Figure 2A:
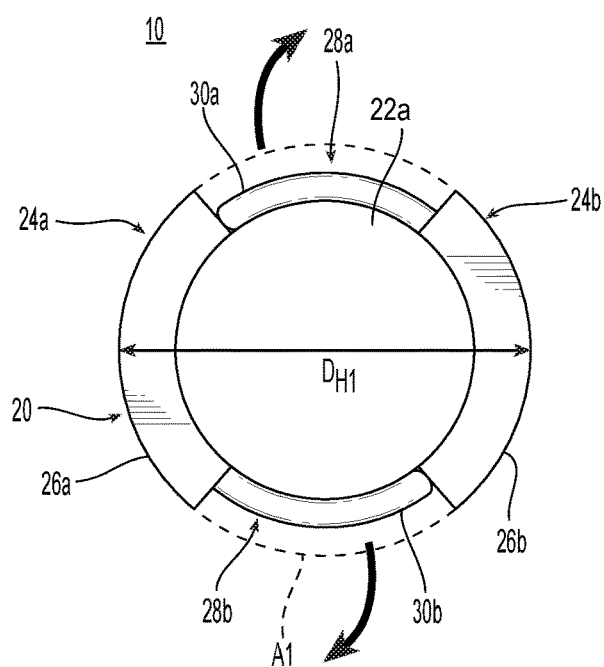
FIG. 2A is a top plan view of the surgical fastener of FIG. 1 in a first configuration.
Figure 2B:
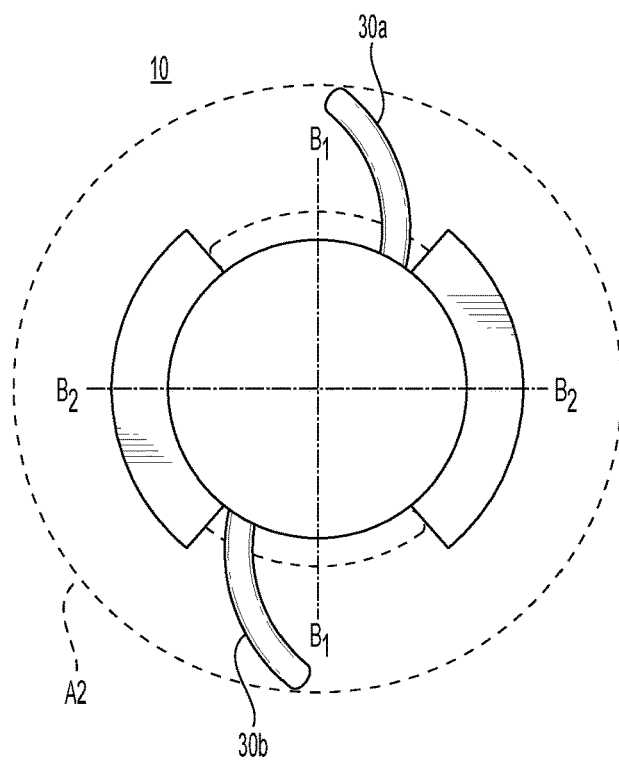
FIG. 2B is a top plan view of the surgical fastener of FIG. 1 in a second configuration.

With reference now to the drawings wherein like numerals represent like elements throughout the several views, the presently-disclosed surgical fastener will be described. As used herein, the term "operator" may refer to any user, e.g., a nurse, doctor, or clinician, of the presently-disclosed surgical fastener. Further, the term "distal" refers to that portion of the surgical fastener, or component thereof, further from the operator while the term "proximal" refers to that portion of the surgical fastener, or component thereof, closer to the operator.

Referring initially to FIGS. 1, 2A, 2B, 3A, and 3B, a surgical fastener 10 according to an embodiment of the present disclosure is shown. Surgical fastener 10, as shown, may have a substantially conical configuration and defines a longitudinal axis "A." Surgical fastener 10 includes a head section 20 and a tissue snaring section 40.

Head section 20 has a substantially flat, disc-like profile that has a proximal surface 22a and a distal surface 22b. Head section 20 defines a first transverse axis "$B_1$" and a second transverse axis "$B_2$" that are each orthogonal to the longitudinal axis "A" and to each other. Head section 20 comprises two opposing threaded sections 24a, 24b disposed that protrude radially outwardly from the head section 20. Opposing threaded sections 24a, 24b may have a tapered configuration and include threads 26a, 26b, respectively, that are configured for arm with portions of a delivery device (e.g., a surgical tacker instrument), as will be described further below. A pair of radial gaps 28a, 28b are defined between the threaded sections 24a, 24b of head section 20, and may be positioned for arm with other portions of a delivery device, as will be described further below.

A pair of arm members 30a, 30b are disposed within the respective radial gaps 28a, 28b of the head section 20. Arm members 30a, 30b are integrally formed with and extend from head section 20 in a cantilevered fashion.

Arm members 30a, 30b may have an arcuate profile, as shown, and may lie substantially parallel to the proximal surface 22a of the head section 20. Arm members 30a, 30b may be disposed at a longitudinal position between the proximal surface 22a and the distal surface 22b of the head section 20. Arm members 30a, 30b are configured for pivotal movement with respect to the head section 20. Arm members 30a, 30b have a flexible and/or resilient configuration, and accordingly may define a spring constant. Arm members 30a, 30b are biased toward a radially-outward or cantilevered configuration, as will be described further below. In some embodiments, arm members 30a, 30b may include friction-enhancing features, e.g., grooves, ridges, or spikes formed thereon. Additionally, arm members 30a, 30b may be formed of a material sufficient to resist deformation thereof.

Arm members 30a, 30b may be monolithically formed with the outer surface of head section 20. In some embodiments, arm members 30a, 30b may be separable components that are attached to the remainder of head section 20 via, e.g., brazing or welding, a living hinge, or adhering.

In this manner, arm members 30a, 30b are configured to pivot and flex or swing radially outwardly with respect to the remainder of head section 20. Turning to FIG. 4, the movement of arm members 30a, 30b allows surgical fastener 10 to transition between a first, undeployed condition, in which arm members 30a, 30b are approximated radially-inwardly toward the remainder of head section 20, and a second, deployed configuration, in which arm members 30a, 30b are disposed radially outwardly with respect to the remainder of head section 20. As the arm members 30a, 30b are disposed within the respective radial gaps 28a, 28b, arm members 30a, 30b may define a radius of curvature that approximates the radius of curvature defined by the outer surface of the head section 20 within the radial gaps 28a, 28b to accommodate folding into the second, deployed configuration of surgical fastener 10.

The distal surface of head section 20 is formed onto the proximal end 42 of tissue snaring section 40. Tissue snaring section 40, as shown, may have a substantially conical profile that tapers from its proximal end 42 to a distal tip 44. Tip 44 defines a pointed surface that is configured for penetration of, e.g., a mesh and/or tissue, as will be described further below. Tissue snaring section 40 further includes a thread 46 formed therearound. Tissue snaring section 40 may define a maximum diameter "$D_S$" (FIG. 3B) that is less than an outer diameter "$D_{H1}$" defined by the head section 20, as shown. In this manner, head section 20 may form a flanged surface protruding radially away from the proximal end 42 of the tissue snaring section 40.

Thread 46 follows a generally helical, distally-downward path along tissue snaring section 40. Thread 46 may have a first terminus at the proximal end 42 of tissue snaring section 40, and may have a second terminus at the distal tip 44 of tissue snaring section 40. In some embodiments, thread 46 may have first and second terminuses disposed between the proximal and distal ends 42, 44 of tissue snaring section 40. Thread 46 may have any desirable configuration suitable for a surgical fastener, e.g., single-thread or double-thread. Thread 46 may be formed onto the tissue snaring section 40 by any suitable manner, e.g., etching or molding such that the thread 46 is monolithically formed with the tissue snaring section 40, or thread 46 may be attached to the tissue snaring section 40 by adhesion, brazing, or welding.

It will be understood that surgical fastener 10 may have any configuration suitable for its intended purpose. An exemplary surgical fastener is disclosed in U.S. Pat. No. 8,414,627 to Corradi, et al., the entire contents of which are incorporated by reference herein.

Figure 5:
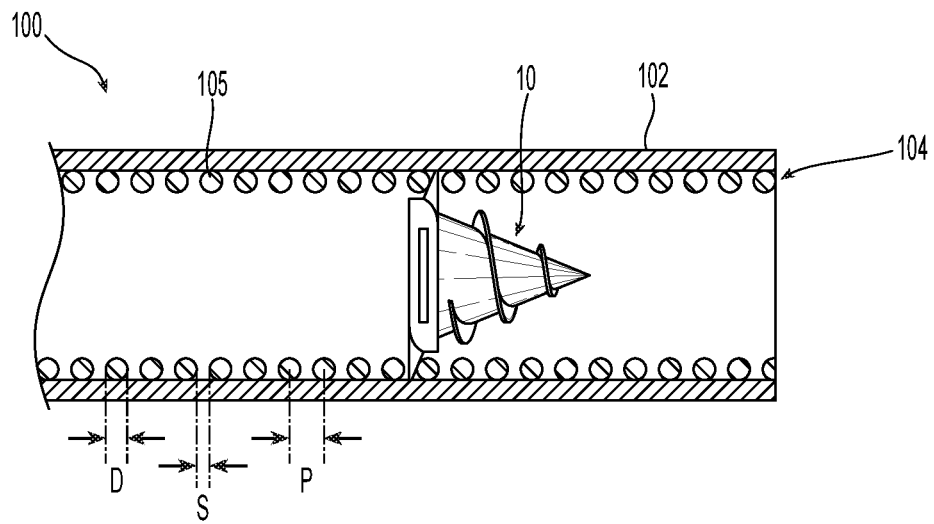
FIG. 5 is a side, cut-away view of a delivery device with the surgical fastener of FIG. 1 disposed therein.
Figure 6:
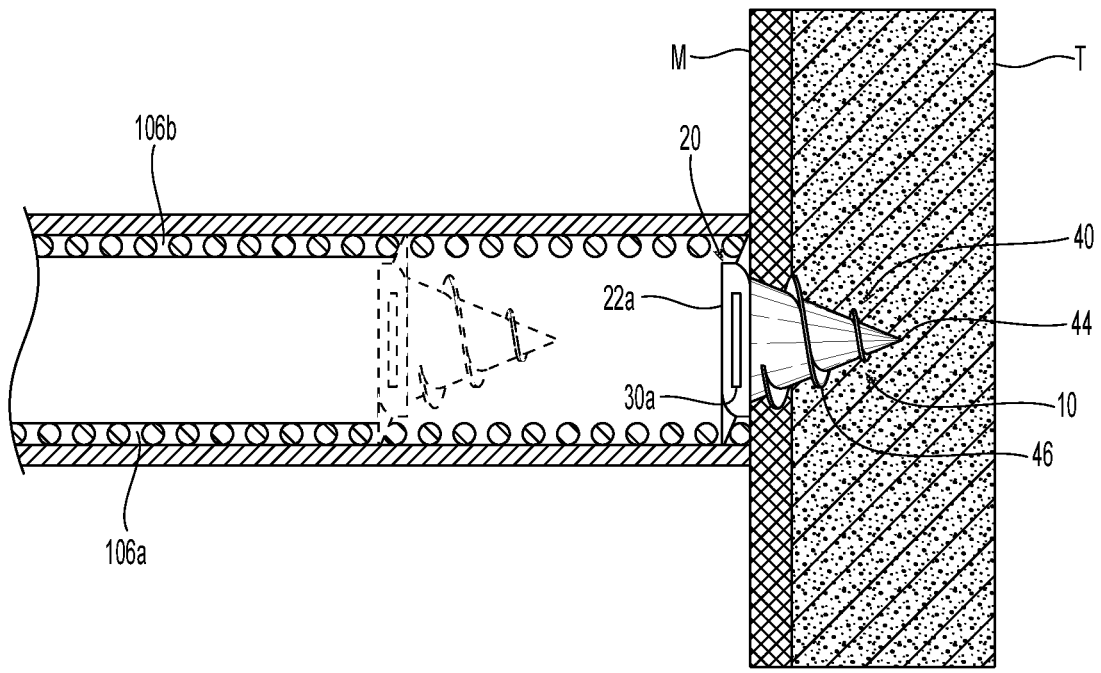
FIG. 6 is a side, cut-away view of the delivery device of FIG. 4 advancing the surgical fastener of FIG. 1 through a mesh and into tissue.

Turning now to FIG. 5, a distal portion of a delivery device, generally designated as 100, is shown. Delivery device 100 may have any suitable configuration, such as a surgical fastener applier or tacker instrument, to advance surgical fasteners 10 through a mesh "M" and into tissue "T" below. A suitable delivery device is described in detail in U.S. Pat. No. 8,114,099 to Shipp, the entire content of which is incorporated by reference herein.

Delivery device 100 may include an outer tube portion 102 and a coil member 104 disposed therein. Coil member 104 is a substantially resilient member that may have a flexibility profile such that the outer tube portion 102 of the delivery device 100 is biased to return to a resting position under a bending load. Coil member 104 is fixedly disposed within the outer tube portion 102 and may be attached to the interior surface of outer tube portion 102 in any suitable manner, e.g., adhesion brazing or welding. Coil member 104 includes a body 105 having a diameter "D" and being disposed in a helically wound configuration that defines pitch "P."

Surgical fastener 10 may be loaded into delivery device 100 in any suitable manner, e.g., a stack or column. The outer tube portion 102 of delivery device 100 is dimensioned such that the arm members 30a, 30b are constrained in the first, undeployed condition by the interior surface of the outer tube portion 102. Successive winds of the coil member 104 are disposed such that longitudinal spaces "S" are defined between adjacent winds of the coil member 104. In this manner, the coil member 104 has a configuration such that the opposing threaded portions 24a, 24b of the surgical fastener 10 may be disposed within the spaces "S" between adjacent winds of the body 105 of coil member 104.

Delivery device 100 may also include a pair of radially-opposed tines 106a, 106b that extend longitudinally within the interior of outer tube portion 102 to engage the surgical fastener 10. Specifically, radially-opposed tines 106a, 106b are dimensioned such that the each radially-opposed tine 106a, 106b may be disposed within the respective gaps 28a, 28b defined between the opposing threaded portions 24a, 24b of surgical fastener 10. (FIG. 1). Accordingly, the arm members 30a, 30b of the surgical fastener 10 disposed within the respective radial gaps 28a, 28b of the surgical fastener 10 may be configured and arranged such that the arm members 30a, 30b are radially offset from the opposing threaded portions 24a, 24b of the surgical fastener 10 such that a space is defined for the respective tines 106a, 106b to extend therethrough.

In use, the delivery device 100 is actuated such that the tines 106a, 106b rotate within the outer tube portion 102. As the opposing threaded portions 24a, 24b of the surgical fastener 10 are threadably engaged with the longitudinal spaces "S" defined by the coil member 104, rotation of the tines 106a, 106b urges the opposing threaded portions 24a, 24b to turn within the coil member 104 about the longitudinal axis "A" (FIG. 1), which causes distal advancement of the surgical fastener 10 through the outer tube portion 102 of delivery device 100 along a helical path defined by the body 105 of coil member 104. As the surgical fastener 10 approaches the distal end of the delivery device 100, the tissue snaring section 40 and distal tip 44 of the surgical fastener 10 protrude from the outer tube portion 102. Further arm and rotation by the tines 106a, 106b causes the surgical fastener 10 to penetrate and advance through, e.g., mesh "M" and into tissue "T."

Mesh "M" may be any suitable mesh material configured to cover a desirable portion of tissue, e.g., a hernial defect. Tissue "T" may be any external or internal section of tissue, e.g., an abdominal wall.

Figure 7:
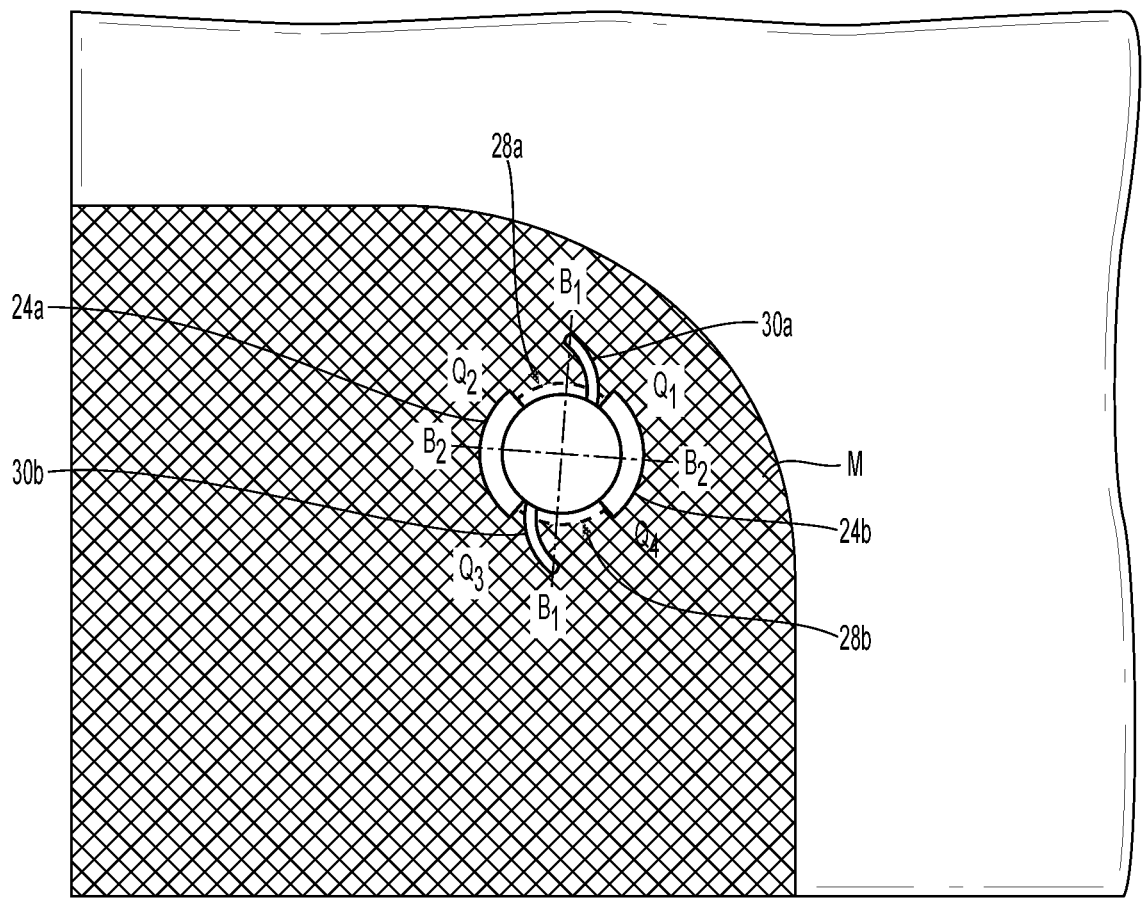
FIG. 7 is a top plan view of the surgical fastener deployed into a mesh as shown in FIG. 6.

Turning now to FIG. 7, deployment of the surgical fastener 10 will be described. Once the head section 20 of the surgical fastener 10 advances past the distal end of the outer tube 102 (FIG. 5) of delivery device 100, the arm members 30a, 30b disposed between the opposing threaded head sections 24a, 24b are free to flex radially outwardly. Accordingly, the arm members 30a, 30b pivot about their point of attachment to the head section 20 of surgical fastener 10, and experience a degree of rotation away from the head section 20. Each arm member 30a, 30b may pivot through, e.g., between about 0 degrees and about 180 degrees measured from the point of attachment of each respective arm member 30a, 30b to the head section 20 of the surgical fastener 10. Accordingly, from a top plan view of the surgical fastener 10, each respective arm member 30a, 30b may be disposed in a respective first quadrant $Q_1$ and third quadrant $Q_3$ measured along the pair of transverse axes "$B_1$," "$B_2$" defined along the proximal surface of head section 20 of surgical fastener 10. Accordingly, each respective opposing threaded section 24a, 24b may be disposed in a respective second quadrant $Q_2$ and fourth quadrant $Q_4$. It will be understood that surgical fastener 10 may have any configuration such that any of the opposing threaded sections 24a, 24b or arm members 30a, 30b may be disposed in any of quadrants $Q_1$, $Q_2$, $Q_3$, $Q_4$.

Accordingly, as the arm members 30a, 30b are deployed radially outwardly with respect to the head section 20 of surgical fastener 10, surgical fastener 10 transitions from the first, undeployed condition, in which surgical fastener 10 defines a first arm area "A1" determined by the maximum outer diameter "$D_{H1}$" of the head section 20 of surgical fastener 10, and the second, deployed condition, in which surgical fastener 10 defines a second arm area "A2" determined by the maximum outer diameter "$D_{H2}$" of the head section 20, measured between the radially outward ends of the arm members 30a, 30b.

With the arm members 30a, 30b disposed radially outwardly in the second, deployed configuration, a greater amount of area of the mesh "M" is engaged by the surgical fastener 10 and compressed against tissue "T." Accordingly, arm members 30a, 30b facilitate the secure arm of a mesh "M" against tissue "T," and provide enhanced mesh retention properties, e.g., for long-term use or to minimize disarm of the surgical fastener 10 from the mesh "M" due to shifting of the tissue "T" or other external loads applied to the surgical fastener 10, mesh "M," or tissue "T." In this manner, the configuration of surgical fastener 10 provides optimal mesh retention properties such that a smaller number of surgical fasteners 10 may be employed as compared to surgical fasteners devoid of arm members 30a, 30b. Further, by providing the head section 20 of surgical fastener 10 with arm members 30a, 30b, optimal mesh retention properties are provided without increasing the portion of the tissue snaring section 40 inserted into the tissue "T."

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:
1. A surgical system comprising:
a delivery device; and
a surgical fastener loaded within the delivery device, the surgical fastener including:
a head section including an arm member pivotably disposed on an outer surface of the head section, the arm member configured to pivot radially outward from the outer surface of the head section, wherein a distal surface of the arm member extends along a first plane spaced apart from a second plane defined by a distal surface of the head section, the arm member including a fixed end and a free end, wherein the fixed end is connected to the head section between a distal end and a proximal end of the head section; and a tissue snaring section defining a longitudinal axis and extending away from the head section, the tissue snaring section having an outer surface defining at least one helical thread.

2. The surgical system of claim 1, wherein the head section of the surgical fastener includes a threaded section.

3. The surgical system of claim 2, wherein the arm member is disposed radially adjacent to the threaded section of the head section.

4. The surgical system of claim 1, wherein the delivery device is configured to maintain the arm member in a radially inward position relative to the head section while the surgical fastener is supported within the delivery device.

5. The surgical system of claim 4, wherein the arm member is biased radially outward relative to the outer surface of the head section.

6. The surgical system of claim 4, wherein the delivery device includes a rotatable tine that maintains the arm member in the radially inward position while rotating the surgical fastener.

7. The surgical system of claim 1, further comprising a mesh configured to receive the surgical fastener upon ejection of the surgical fastener from the delivery device.

8. The surgical system of claim 7, wherein the arm member of the surgical fastener is configured to prevent the head section of the surgical fastener from passing through the mesh.

9. A surgical system comprising:
a delivery device; and
a surgical fastener loaded within the delivery device, the surgical fastener including:
a head section including opposing threaded portions configured to engage spaced apart radially-opposed tines of the delivery device to advance the surgical fastener through the delivery device, the head section including an arm member pivotably disposed on an outer surface of the head section, the arm member configured to pivot radially outward from the outer surface of the head section, wherein a distal surface of the arm member extends along a first plane spaced apart from a second plane defined by a distal surface of the head section, the arm member including a fixed end and a free end, wherein the fixed end is connected to the head section between a distal end and a proximal end of the head section; and
a tissue snaring section defining a longitudinal axis and extending away from the head section, the tissue snaring section having an outer surface defining at least one helical thread.

10. The surgical system of claim 9, wherein the delivery device is configured to maintain the arm member in a radially inward position relative to the head section while the surgical fastener is supported within the delivery device.

11. The surgical system of claim 9, wherein the arm member is biased radially outward relative to the outer surface of the head section.

12. The surgical system of claim 9, further comprising a mesh configured to receive the surgical fastener upon ejection of the surgical fastener from the delivery device.

13. The surgical system of claim 12, wherein the arm member of the surgical fastener is configured to prevent the head section of the surgical fastener from passing through the mesh.

14. A surgical fastener comprising:
a head section including an arm member pivotably disposed on an outer surface of the head section, the arm member configured to pivot radially outward from the outer surface of the head section, wherein a distal surface of the arm member extends along a first plane spaced apart from a second plane defined by a distal surface of the head section, the arm member including a fixed end and a free end, wherein the fixed end is connected to the head section between a distal end and a proximal end of the head section; and
a tissue snaring section defining a longitudinal axis and extending away from the head section, the tissue snaring section having an outer surface defining at least one helical thread.

15. The surgical system of claim 14, wherein the head section of the surgical fastener includes a threaded section.

16. The surgical system of claim 15, wherein the arm member is disposed radially adjacent to the threaded section of the head section.

17. The surgical system of claim 14, wherein the arm member is biased radially outward relative to the outer surface of the head section.

* * * * *